United States Patent
Adamson et al.

(10) Patent No.: US 11,542,223 B1
(45) Date of Patent: Jan. 3, 2023

(54) PROCESS FOR PREPARING DI- AND POLYAMINES OF THE DIPHENYL METHANE SERIES

(71) Applicants: Covestro LLC, Pittsburgh, PA (US); Covestro Deutschland AG, Leverkusen (DE)

(72) Inventors: Richard Adamson, Leichlingen (DE); Dolan OConnor, Baytown, TX (US); Stefan Wershofen, Mönchengladbach (DE)

(73) Assignees: Covestro LLC, Pittsburgh, PA (US); Covestro Deutschland AG, Leverkusen (DE)

( * ) Notice: Subject to any disclaimer, the term of this patent is extended or adjusted under 35 U.S.C. 154(b) by 0 days.

(21) Appl. No.: 17/870,043

(22) Filed: Jul. 21, 2022

(51) Int. Cl.
*C07C 209/78* (2006.01)

(52) U.S. Cl.
CPC ................................. *C07C 209/78* (2013.01)

(58) Field of Classification Search
CPC ... C07C 209/78; C07C 209/82; C07C 209/84; C07C 209/86; C07C 211/50; C07C 211/51; C07C 209/68
See application file for complete search history.

(56) References Cited

U.S. PATENT DOCUMENTS

| | | | |
|---|---|---|---|
| 4,189,443 A | 2/1980 | Eifler et al. | |
| 5,286,760 A | 2/1994 | Bolton et al. | |
| 5,310,769 A | 5/1994 | Koenig et al. | |
| 6,031,136 A | 2/2000 | Renbaum et al. | |
| 8,318,971 B2* | 11/2012 | Pohl | C25B 15/08 560/347 |
| 8,431,746 B2* | 4/2013 | Jacobs | C07C 209/84 564/333 |
| 8,871,979 B2* | 10/2014 | Mitchell | C07C 209/78 564/330 |
| 9,279,029 B2* | 3/2016 | Mueller | C08G 18/7657 |
| 9,309,184 B2* | 4/2016 | Knauf | B01D 17/085 |
| 9,416,094 B2* | 8/2016 | Knauf | C07C 209/78 |
| 9,701,617 B2* | 7/2017 | Wershofen | C07C 209/78 |
| 9,815,769 B2* | 11/2017 | Knauf | C08G 73/0266 |
| 10,125,091 B2* | 11/2018 | Knauf | C07C 209/78 |
| 10,173,969 B2* | 1/2019 | Jaeger | C12P 13/001 |
| 2005/0014975 A1 | 1/2005 | Strofer et al. | |
| 2006/0224018 A1 | 10/2006 | Hagen et al. | |
| 2006/0287555 A1 | 12/2006 | Hagen et al. | |
| 2007/0179316 A1 | 8/2007 | Pohl et al. | |
| 2017/0107171 A1 | 4/2017 | Knauf et al. | |
| 2017/0137367 A1* | 5/2017 | Knauf | C07C 209/86 |

FOREIGN PATENT DOCUMENTS

| | | | |
|---|---|---|---|
| DE | 238042 A1 | 8/1986 | |
| DE | 295628 A5 | 11/1991 | |
| EP | 0451442 A2 | 10/1991 | |
| EP | 1167343 A1 * | 1/2002 | C07C 209/78 |
| EP | 1167343 A1 | 1/2002 | |
| EP | 1257522 B1 | 11/2002 | |
| EP | 1652835 A1 | 5/2006 | |
| EP | 1813598 B1 | 8/2007 | |
| EP | 2103595 A1 | 9/2009 | |
| GB | 1365454 A | 9/1974 | |

OTHER PUBLICATIONS

B. Amini et al., Kirk-Othmer Encyclopedia of Chemical Technology, Aniline and Its Derivatives, 783-809 (2003) (Year: 2003).*

* cited by examiner

*Primary Examiner* — Alexander R Pagano
(74) *Attorney, Agent, or Firm* — Donald R. Palladino

(57) ABSTRACT

The present invention relates to a process for preparing di- and polyamines of the diphenyl methane series. More specifically, the process comprises reacting aniline and formaldehyde by (1a) mixing aniline with hydrochloric acid to form aniline hydrochloride, and (1b) mixing the aniline hydrochloride with a first portion of aqueous formaldehyde; or (1c) mixing aniline with a first portion of aqueous formaldehyde to form an aminal, and (1d) mixing the aminal with hydrochloric acid; to obtain a first reaction product; (2) converting the first reaction product to a second reaction product comprising di- and polyamines of the diphenyl methane series in a cascade of 4 to 25 reaction zones arranged in series, wherein a second portion of aqueous formaldehyde is added to the second of the reaction zones, in which second reaction zone the temperature is equal to or up to 20° C. higher than the temperature in the first reaction zone, and wherein the temperature consecutively increases from the third to the last of the reaction zones, the temperature in the third of the reaction zones being from 15° C. to 50° C. higher than in the second of the reaction zones, and (3) working-up the second reaction product to obtain the di- and polyamines of the diphenyl methane series.

21 Claims, No Drawings

PROCESS FOR PREPARING DI- AND POLYAMINES OF THE DIPHENYL METHANE SERIES

FIELD

The present invention relates to a process for preparing di- and polyamines of the diphenyl methane series. More specifically, the process comprises reacting aniline and formaldehyde by (1a) mixing aniline with hydrochloric acid to form aniline hydrochloride, and (1b) mixing the aniline hydrochloride with a first portion of aqueous formaldehyde; or (1c) mixing aniline with a first portion of aqueous formaldehyde to form an aminal, and (1d) mixing the aminal with hydrochloric acid; to obtain a first reaction product; (2) converting the first reaction product to a second reaction product comprising di- and polyamines of the diphenyl methane series in a cascade of 4 to 25 reaction zones arranged in series, wherein a second portion of aqueous formaldehyde is added to the second of the reaction zones, which second reaction zone is at a temperature that is equal to or up to 20° C. higher than the temperature in the first reaction zone, and wherein the temperature consecutively increases from the third to the last of the reaction zones, the temperature in the third of the reaction zones being from 15° C. to 50° C. higher than in the second of the reaction zones, and (3) working-up the second reaction product to obtain the di- and polyamines of the diphenyl methane series.

BACKGROUND

Diamines and polyamines of the diphenylmethane series (MDA) are understood to be amines and mixtures of amines of the following type:

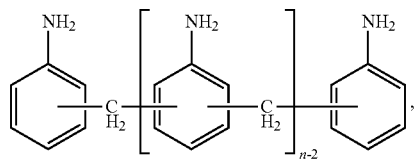

wherein n stands for a natural number 2.

The term monomeric MDA (MMDA) is used herein for compounds and mixtures of compounds with n=2 (=diamines of the diphenylmethane series) and the term polymeric MDA (PMDA) is used herein for compounds and mixtures of compounds with n>2 (=polyamines of the diphenylmethane series) are also conventional. For the sake of simplicity, mixtures of compounds in which compounds with n=2 and n>2 occur side by side are conventionally grouped together under the term MDA (=diamines and polyamines of the diphenylmethane series). These diamines and polyamines of the diphenylmethane series are important intermediates in the production of diisocyanates and polyisocyanates of the diphenylmethane series (MDI), which are obtained by phosgenation of MDA.

The continuous, discontinuous or semi-continuous preparation of diamines and polyamines of the diphenylmethane series is described in numerous publications and patents. In the processes that are employed in industry, MDA is conventionally prepared by reacting aniline and formaldehyde in the presence of an acid catalysts, the acid catalyst conventionally being neutralized at the end of the process by addition of a base, the reaction mixture being separated into an organic and an aqueous phase and the organic phase being sent to the final processing stages, such as for example removal of excess aniline by distillation. The initial reaction of aniline and formaldehyde can be carried out by mixing aniline with hydrochloric acid to form aniline hydrochloride, which is then mixed with formaldehyde. It is also possible to mix aniline and formaldehyde in the absence of the acid catalyst followed by mixing the aminal formed thereby with hydrochloric acid. In either case a first reaction product is formed which is converted to the desired MDA in a rearrangement step at elevated temperatures.

Common to all of the processes described in the literature for preparing MDA by reacting aniline and formaldehyde in the presence of an acid catalyst is the fact that chromophores or their precursors are formed during the reaction which discolor the MDI that is produced downstream by phosgenation of the obtained MDA. During neutralization of the acid catalyst and removal of the aniline that is used in excess in the reaction, these chromophores or their precursors are not or not adequately reduced or removed, and during the subsequent phosgenation of the MDA to form the corresponding diisocyanates and polyisocyanates and their subsequent processing (separation of the solvent, separation of monomeric MDI (=MMDI)), they commonly lead to darkly colored products which in turn result in polyurethane foams having a yellowish or greyish discoloration or to other discolored polyurethane (PU) materials. Although the natural color of the diisocyanates and polyisocyanates has no negative influence on the mechanical properties of the polyurethanes that are produced therefrom, light-colored products are preferred because of their good variability in the manufacturer's production process, for example in terms of visibility through thin top coats and colored design possibilities.

Another problem encountered in the context of industrial MDA production is the formation of undesirable secondary products, in particular N-methylated compounds. As secondary amines, these cannot be converted into isocyanates; rather, they pose problems in that they form secondary carbamic acid chlorides upon phosgenation and thus contribute to the formation of hydrolyzable chlorine compounds in the desired MDI. It is generally believed that N-methyl-MDA is formed as a result of a side reaction between aniline and formaldehyde that produces N-methylaniline, and this by-product reacts, like aniline, with formaldehyde to become N-methyl-MDA.

There has been no shortage of attempts to reduce the discoloration of MDA and/or the amount of N-methylated secondary products produced:

US 2007/179316 A1 aims at improving the coloration of MDI obtained by phosgenation of the mixtures of diamines and polyamines that are formed by reacting aniline with formalin in the presence of acid catalysts or of the isocyanates and polyurethanes produced from them. To this end, a process is described that uses an aniline containing less than 3 wt. % of diamines and polyamines of the diphenylmethane series, based on the weight of the aniline used, in the preparation of diamines and polyamines.

US 2005/0014975 A1 relates to a process for preparing methylenedianiline by reacting aniline with formaldehyde in the presence of acid catalysts which aims at minimizing the N-methyl-MDA content as an unwanted byproduct. Such an MDA should be used, in particular, in an improved process for preparing methylenebis(phenyl isocyanate) (MDI), which should make accessible an MDI having improved properties, in particular a low chlorine content and/or a light color, in particular in the crude MDI which, in addition to the monomeric MDI, also comprises polymeric MDI. To this end, a semicontinuous process is disclosed, which encompasses introducing aniline with or without acid catalyst, feeding formaldehyde with or without acid catalyst through a mixing element into a circuit in which aniline with or without acid catalyst and with or without previously added formaldehyde is circulated and, after feeding in at least 50% of the total amount of formaldehyde to be fed in, heating the reaction mixture to a temperature above 75° C.

DD 295 628 A5 relates to a method for the discontinuous production of methylenedianiline/polyamine mixtures used in the manufacture of aromatic isocyanates. In one embodiment, formaldehyde is mixed with a circulated reaction mixture in the proportion of 1:10 to 1:300 with turbulence corresponding to a Reynolds number >10,000, whereby 55% to 85% of the amount of formaldehyde are added at a temperature of ≤40° C. and 45% to 15% of the amount of formaldehyde are added at 60° C. to 80° C. within at least 10 min to 30 min. In another embodiment, 70% to 90% of the total amount of formaldehyde are added under adiabatic reaction conditions within at least 10 min to 30 min and 30% to 10% of the amount of formaldehyde are added in at least 10 min to 30 min to the reaction mixture.

EP 0 451 442 A2 relates to a process for continuously preparing a methylene-crosslinked polyarylamine. More specifically, the disclosure is directed to a process for the continuous preparation of a methylene-crosslinked polyarylamine from aniline and formalin by the use of a multi-stage reactor, the aforesaid process being characterized by reacting aniline with formalin in the presence of hydrochloric acid under conditions that formalin is divided and placed in 3 or more stages. Hydrochloric acid is used in a molar ratio of from 0.1 to 0.5 mole per mole of aniline; aniline is used finally in a molar ratio of from 1.5 to 4.0 moles per mole of formalin. The reaction temperatures in the first stage, the second stage, the third et seq. stages and the final stage are adjusted to 20-50° C., 40-70° C., 50-90° C. and 110° C. or more, respectively; and molar ratios of water to aniline of 1.3-2.5 in the first stage, 1.9-5.0 in the second stage, and 2.4-5.7 in the third et seq. stages are used.

DD 238 042 A1 relates to a process for the production of aromatic isocyanates which are used in rigid foam production by phosgenation of amines of the diphenylmethane series through acidic condensation of aniline and formaldehyde. Methylenedianilines and their higher oligomers, which are characterized by a low content of N-methylation products, are produced such that formaldehyde is added to an aniline hydrochloride stream continuously in 2 installments. After the first addition of formaldehyde, the product stream is cooled to <50° C.

U.S. Pat. No. 5,286,760 relates to a process for preparing a reaction product containing methylene di(phenylamine) comprising reacting aniline with formaldehyde, in the presence of a low level of an acid which is sufficient to catalyze the reaction at an initial and/or condensation stage of said reaction and produce methylene di(phenylamine)intermediates; providing a reaction mixture at the condensation stage with an acid content which is at or below the initial acid level at the end of the condensation stage, and holding the reaction mixture at a high temperature which is sufficient to effect a rearrangement of the intermediates to produce a reaction product containing methylene di(phenylamines) and low levels of impurities.

U.S. Pat. No. 5,310,769 describes a process for production of polyamines of the diphenylmethane series through a condensation reaction of aniline with formaldehyde in the presence of an acid catalyst, neutralization of the acid catalyst after reaction completion, and distillation of the resultant polyamine mixture. More specifically, the process comprises the following sequence of steps: a) aniline is reacted with formaldehyde in a mole ratio of 1.5:1 to 10:1 at temperatures between 10 and 150° C., b) an acid catalyst is thereafter added to the reaction mixture at a mole ratio of aniline to acid catalyst of from 2:1 to 100:1 (corresponding to a protonation degree of 1 to 50%) and the temperature is from 10 to 150° C., and wherein the water formed during the condensation reaction is removed either before step b) or after step b), c) the temperature of the mixture obtained from b) is increased by at least 40° C. in no more 15 minutes, and thereafter, if necessary, heating of the mixture is continued to a final temperature between 105 and 200° C., with the proviso that the reaction time is from 10 to 300 minutes after the temperature increase, and d) the reaction mixture from c) is distilled after neutralization of the acid catalyst.

GB 1 365 454 describes a process for the preparation of aromatic polyamines wherein one or more aromatic amines are condensed with formaldehyde in the presence of acid catalysts in which the reaction is carried out in two stages, the first stage being carried out in the presence of a volatile solvent, and under reduced pressure, the vacuum being such that the temperature of the reaction mixture does not rise above 40° C., and the second stage being carried out at a temperature of at least 80° C.

U.S. Pat. No. 4,189,443 relates to a process for the preparation of a polyamine wherein an aromatic amine and formaldehyde are condensed in the presence of an acidic catalyst. More specifically, the process comprises boiling the reaction mixture under reflux at a temperature of at least 60° C. whereby vapors from the mixture are condensed and returned to the mixture, adding an aqueous formaldehyde solution to the said condensed vapors and recovering the resulting polyamine.

US 2006/224018 A1 relates to a process for the preparation of MDA which aims at preventing or suppressing the formation of undesirable isomers, homologues or by-products. The process comprises combining a first portion of the aniline to be reacted with acid catalyst and a second portion of the aniline to be reacted with formaldehyde. The first and second portions of aniline are then combined and reacted.

US 2006/287555 A1 relates to a process for the acid-catalyzed preparation of polyamines of the diphenylmethane series. This process comprises a) reacting aniline and formaldehyde in a molar ratio of 1.5:1 to 6:1, at temperatures of 20° C. to 100° C., in which the water content in the acid reaction mixture is <20 wt. % and a degree of protonation of <15% is established, and b) increasing the temperature of the reaction mixture to 110° C. to 250° C. when the ratio of the weight contents of p-aminobenzylaniline to 4,4'-MDA in the acid reaction mixture falls below a value of 1.00.

EP 1 167 343 A1 describes the production of an aromatic polyamine mixture comprising 4,4'-methylenedianiline (4,4'-MDA) and higher homologs, by reacting aniline with formaldehyde, comprising using a split stream of formaldehyde which is mixed with 2,2'-methylenedianiline (2,2'-MDA) and 2,4'-methylenedianiline (2,4'-MDA) by-products and recycled to a rearrangement zone. More specifically, the process is carried out by: (a) reacting aniline with formaldehyde in a plant comprising a mixing zone, a condensation zone, a rearrangement zone and optionally a post-reaction zone, and (b) separating 2,2'-MDA and 2,4'-MDA from the crude product which comprises splitting the formaldehyde feed into at least two parts, with one part being supplied to the condensation zone and one part being mixed with the 2,2'-MDA and 2,4'-MDA and recycled to the rearrangement zone.

U.S. Pat. No. 6,031,136 encompasses a process for preparing a reaction product containing methylene diphenylamine, comprising reacting aniline and formaldehyde in the presence of an acid catalyst; reducing the acid level of the resulting reaction mixture during digestion of the reaction mixture, followed by completely neutralizing the reaction product after further digestion.

US 2017/107171 A1 relates to a process for preparing diamines and polyamines of the diphenylmethane series (MDA) from aniline and formaldehyde, in which care is taken during the start-up procedure to ensure that there is a sufficient excess of aniline over formaldehyde which is at least 105% of the molar ratio of aniline to formaldehyde wanted for the target formulation of the MDA to be produced. It is disclosed that at low intended molar ratios of aniline to formaldehyde (=A/F$_{target}$, i.e. the molar ratio of aniline to formaldehyde (CH2O) in the target formulation), there is a risk of deposition of solids ("aminal solids") in the aminal separator. A "formalin split" in which only part of the formalin required for attaining the A/F$_{target}$ value is introduced into the aminal reaction and the remaining formalin is fed into the reaction mixture immediately before, at the same time as or after the introduction of acid makes it possible to work with a sufficiently high molar ratio of aniline to formaldehyde in the aminal section in order to prevent solids formation. US 2017/107171 A1 remains silent regarding any impact of the "formalin split" on MDA and/or MDI quality and regarding the process parameters of the "formalin split".

SUMMARY

Despite the many endeavors undertaken in this field of research, there is still room for further improvements of the MDA and/or MDI quality, e.g. MDI color and/or chlorine content.

Taking account of this need, the present invention provides:

A process for preparing di- and polyamines of the diphenyl methane series, comprising:
(1) Reacting aniline and formaldehyde by
  (1a) mixing aniline with hydrochloric acid to form aniline hydrochloride, and
  (1b) mixing the aniline hydrochloride with a first portion of aqueous formaldehyde;
  or
  (1c) mixing aniline (in the absence of hydrochloric acid) with a first portion of aqueous formaldehyde to form an aminal, and
  (1d) mixing the aminal with hydrochloric acid;
to obtain a first reaction product;
(2) converting the first reaction product to a second reaction product comprising di- and polyamines of the diphenyl methane series in a cascade of 4 to n reaction zones arranged in series, n being a natural number of from 4 to 25 (with n being preferably 15, corresponding to a cascade of 4 to 15 reaction zones, n being more preferred 12, corresponding to a cascade of 4 to 12 reaction zones, n being even more preferred 10, corresponding to a cascade of 4 to 10 reaction zones, and n being most preferred 8, corresponding to a cascade of 4 to 8 reaction zones), wherein a second portion of aqueous formaldehyde is added to the second of the n reaction zones, which second reaction zone is at a temperature that is equal to or— preferably—up to 20° C. (preferably up to 10° C., more preferably up to 5° C.) higher than the temperature in the first reaction zone, and wherein the temperature consecutively increases from the third to the n$^{th}$ of the reaction zones, the temperature in the third of then reaction zones being from 15° C. to 50° C. higher than in the second of the n reaction zones,
and
(3) working-up the second reaction product to obtain the di- and polyamines of the diphenyl methane series.

It has surprisingly been found that both, (i) the formation of chromophores or their precursors that eventually lead to discoloration of MDA and/or especially MDI obtained after phosgenation and (ii) the formation of N-methylated secondary products in MDA, can be reduced by splitting the addition of formaldehyde (so called "formalin split") such that a first portion is added in the step of the initial reaction of aniline and formaldehyde and a second portion is added, in the rearrangement step (2), to the second of at least 4 reactors arranged in series and following the temperature regime described above.

As used herein, the term "reaction zone" refers to a region inside a chemical reactor which allows for and is used for controlling the temperature independently of other regions. A reaction zone may just be the entire inner volume of a reactor that is available for carrying out the conversion of the first reaction product to the second reaction product in the liquid phase. It is, however, also possible that several reaction zones are contained in one reactor.

There follows first of all a brief summary of various possible embodiments of the invention:

In a first embodiment of the invention, which can be combined with all other embodiments, the first portion of aqueous formaldehyde comprises 50% to 90% (preferably 50% to 80%, more preferred 50% to 75%) of all formaldehyde ($CH_2O$) used in the process, wherein the percentages refer to moles of formaldehyde ($CH_2O$).

In a second embodiment of the invention, which is a special variant of the first embodiment, the second portion of aqueous formaldehyde comprises 10% to 50% (preferably 20% to 50%, more preferred 25% to 50%) of all formaldehyde ($CH_2O$) used in the process, wherein the percentages refer to moles of formaldehyde ($CH_2O$).

In a third embodiment of the invention, which can be combined with all other embodiments, the molar ratio of aniline to the total amount of formaldehyde used in the process (i.e. the total of formaldehyde contained in all portions of aqueous formaldehyde, in a preferred embodiment with precisely two portions the total of formaldehyde contained in the first portion and the second portion of aqueous formaldehyde) is from 1.5:1 to 10:1.

In a fourth embodiment of the invention, which can be combined with all other embodiments, the aqueous formaldehyde comprises, in relation to its total mass, a proportion by mass of formaldehyde of from 30% to 60%.

In a sixth embodiment of the invention, which can be combined with all other embodiments, the temperature in the first of the n reaction zones is from 30° C. to 70° C., preferably from 40° C. to 65° C., even more preferably 40° C. to 55° C.

In a seventh embodiment of the invention, which is a special variant of the sixth embodiment, the temperature in the first of the n reaction zones is adjusted by evaporating, condensing and (at least partial) feeding-back of water at a pressure lower than ambient pressure.

In an eighth embodiment of the invention, which can be combined with all other embodiments, the temperature in the n$^{th}$ of the n reaction zones is from 120° C. to 200° C.

In a ninth embodiment of the invention, which can be combined with all other embodiments, n equals 15, preferably 12, more preferred 10, and even more preferred 8.

In a tenth embodiment of the invention, which can be combined with any of the first to ninth embodiment, the n reaction zones are located in n reactors.

In an eleventh embodiment of the invention, which can be combined with any of the first to ninth embodiment, the n reactions zones are located in less than n reactors, at least one of the less than n reactors comprising at least two reaction zones which are sequentially run through by the first reaction product.

In a twelfth embodiment of the invention, which can be combined with all other embodiments, after mixing aniline with the first portion of aqueous formaldehyde in (1c), a two-phase mixture is formed which is separated into an aqueous phase and an organic phase comprising the aminal, which organic phase is mixed with hydrochloric acid in (1d).

In a thirteenth embodiment of the invention, which can be combined with any of the first to twelfth embodiment, (1b) or (1d) are carried out in the first reaction zone.

In a fourteenth embodiment of the invention, which can be combined with any of the first to twelfth embodiment, (1b) or (1d) are carried out in an apparatus upstream of the first reaction zone.

In a fifteenth embodiment of the invention, which can be combined with all other embodiments, the addition of the second portion of formaldehyde is carried out 10 minutes to 60 minutes, preferably 15 minutes to 45 minutes, after the initial contacting of aniline hydrochloride with the first portion of aqueous formaldehyde in step (1b) or the initial contacting of the aminal with hydrochloric acid in step (1d).

In a sixteenth embodiment of the invention, which can be combined with all other embodiments, the temperature of the second of then reaction zones is higher (preferably at least 2° C. higher) than the temperature in the first reaction zone.

In a seventeenth embodiment of the invention, which can be combined with all other embodiments, at least step (2), preferably steps (1) and (2), even more preferably steps (1) to (3), is/are carried out continuously.

DETAILED DESCRIPTION

The embodiments indicated above and further possible variants of the invention will be explained in more detail below. All embodiments and further implementation options can be combined with one another in any way, unless the contrary is unambiguously indicated by the context to a person skilled in the art or something different is expressly said.

Step (1) of the process of the invention can be carried out in two variants:

In a first variant, aniline and hydrochloric acid are premixed to give aniline hydrochloride (1a) which is then reacted with the first portion of the aqueous formaldehyde (1b) to give the first reaction product.

In a second variant, aniline is mixed with the first portion of aqueous formaldehyde in the absence of hydrochloric acid (1c) to form an aminal, which is then reacted with hydrochloric acid (1d) to give the first reaction product. The second variant is preferred.

Suitable aniline qualities are described, for example, in EP 1 257 522131, EP 2 103 595 A1 and EP 1 813 598 B1. Preference is given to using technical grade qualities of aqueous solutions of formaldehyde (formalin) with (in relation to the total mass of the solution) a concentration of 30.0% by mass to 60.0% by mass, more preferably 30.0% by mass to 50.0% by mass, of formaldehyde. However, formaldehyde solutions with lower or higher concentrations are also conceivable.

The hydrochloric acid preferably has a concentration of HCl of 25% by mass to 36% by mass, but higher or lower concentrations are also possible. Technical grade hydrochloric acid qualities can in principle be used. It is particularly preferred, however, to use hydrochloric acid qualities as described in EP 1 652 835 A1, i.e. hydrochloric acid that contains less than 0.001% by mass, more preferred less than 0.0005% by mass, even more preferred less than 0.0003% by mass, of metal ions which are divalent and/or more than divalent.

In both variants, it is possible to actually produce the first reaction product only in the first of the n reaction zones of step (2); i.e. it is possible to carry out steps (1b) and (1d) in said first reaction zone.

In both variants, the molar ratio of aniline to the total amount of formaldehyde used in the process (i.e. the total of formaldehyde added in step (1) and in step (2)) is preferably from 1.5:1 to 10:1, more preferably 1.6:1 to 6.0:1, even more preferably 1.7:1 to 5.5:1 and very exceptionally preferably 1.8:1 to 5.0:1. It is preferred that the first portion of aqueous formaldehyde comprises 50% to 90% (preferably 50% to 80%, more preferred 50% to 75%) of all formaldehyde ($CH_2O$) used in the process. It is even more preferred that all of the remainder (10% to 50% (preferably 20% to 50%, more preferred 25% to 50%) of all formaldehyde ($CH_2O$) used in the process) is added as the second portion of aqueous formaldehyde; i.e. it is even more preferred that the formaldehyde is split up in precisely two portions. These percentages refer to moles of formaldehyde ($CH_2O$). In operational practice, it will usually be the case that all (i.e. in the preferred embodiment the precisely two) portions of aqueous formaldehyde are taken from the same storage tank for aqueous formaldehyde, which means that both portions of aqueous formaldehyde solutions have the same concentration of formaldehyde ($CH_2O$). In that case, which is preferred, the percentages given above correspond to the split of formaldehyde in percent by mass. For example, the first portion of aqueous formaldehyde may comprise 50% by mass to 90% by mass (or 50% by mass to 80% by mass, or 50% by mass to 75% by mass), and the second portion of aqueous formaldehyde may comprise 10% by mass to 50% by mass (or 20% by mass to 50% by mass, or 25% by mass to 50% by mass), of the total amount of aqueous formaldehyde to be used in the process.

In the first variant, step (1a) is preferably conducted at temperatures of 20.0° C. to 120.0° C., preferably 40.0° C. to 110.0° C. and more preferably 60.0° C. to 100.0° C. The apparatus used for step (1a) is preferably operated at ambient pressure or under elevated pressure. A pressure slightly above (in particular 10 mbar to 500 mbar above) ambient pressure is preferred.

In the second variant, step (1c) is preferably conducted at temperatures of 20.0° C. to 120.0° C., preferably 40.0° C. to 110.0° C. and more preferably 60.0° C. to 100.0° C., to give the aminal. Besides the aminal, water is produced. Water is also introduced with the formaldehyde (this being used as an aqueous solution), so that the process product of (1c) can actually be two-phasic. It is possible to use such a two-phasic product in its entirety in step (1d). However, it can be advantageous to separate an aqueous phase from the process product of (1c) before reacting the aminal with hydrochloric acid in (1d). This embodiment is particularly preferred if low degrees of protonation (low molar ratios of hydrochloric acid to aniline introduced in (1c)) are to be used in (1d).

The apparatus used for step (1c), the so called aminal reactor is preferably operated at ambient pressure or under elevated pressure. There is preferably a pressure of 1.05 bar to 5.00 bar (absolute), very preferably of 1.10 bar to 3.00 bar (absolute) and most preferably of 1.20 bar to 2.00 bar (absolute). The pressure is maintained by pressure-regulating valves, or in the preferred embodiment with a phase separation between (1c) and (1d), by connecting the off-gas systems of aminal reactor to an overflow from the apparatus used for phase separation, the so called aminal separator. The aminal separator and the outlet for the aqueous phase are preferably heated in order to prevent caking.

In the preferred embodiment, the phase separation of organic aminal phase and aqueous phase is preferably effected at temperatures of 20.0° C. to 120.0° C., more preferably of 40.0° C. to 110.0° C. and most preferably of 60.0° C. to 100.0° C., in each case preferably at ambient pressure or at slightly elevated pressure relative to ambient pressure (elevated by up to 1 bar).

Regardless of the variant used, step (1) is preferably carried out continuously. In a continuous operation mode, a stream of the reactants of step (1a)/(1c) is (for a given reaction period) fed continuously to the respective reaction apparatus, whilst a stream of the products of step (1a)/(1c) is continuously withdrawn therefrom and is continuously fed to the reaction apparatus of step (1b)/(1d). From the latter reaction apparatus, a stream of the products produced therein is continuously removed therefrom (and is guided to the first of the n reaction zones of step (2)).

Step (2) of the present invention concerns the rearrangement of the first reaction product to the second reaction product comprising the desired di- and polyamines of the diphenyl methane series. As mentioned above, it is possible that steps (1b) or (1d), whichever is applicable, is actually carried out in the first of the n reaction zones of step (2). The first reaction product is then formed in-situ in the first reaction zone and immediately subjected to the reaction conditions of the first of the n steps necessary for completion of the rearrangement. It is, however, preferred that steps (1b) or (1d), whichever is applicable, is carried out in an apparatus upstream of the first reaction zone. This can, for example, be a mixing nozzle which mixes aniline hydrochloride with the first portion of aqueous formaldehyde (first variant) or the aminal with hydrochloric acid (second variant), whereby the mixtures produced in the mixing nozzle are guided to the first reaction zone. It is also possible to carry out the mixing step with a dynamic mixer, for example in a (small) stirred vessel.

Step (2) is preferably carried out continuously, just as step (1). A stream of the reactants for the first of the n reaction zones (which is the stream of products of step (1b)/(1d) mentioned above) is (for a given reaction period) added continuously to the respective reaction apparatus, whilst a stream of the products from the first reaction zone is continuously withdrawn therefrom and is continuously added to the second reaction zone. From the second reaction zone, a stream of the products produced therein is continuously removed therefrom and is fed to the third reaction zone etc.

Preferably, the temperature in the first of the n reaction zones is from 30° C. to 70° C., more preferably from 40° C. to 65° C., even more preferably 40° C. to 55° C. The temperature in the first reaction zone is adjusted by cooling, preferably by evaporative cooling. More particularly, water is evaporated from the reaction mixture, condensed and—at least partially—fed back to the reaction zone at a pressure lower than ambient pressure. The temperature can thus easily be adjusted by choice of an appropriate pressure. The first of the n reaction zones is operated without or with additional mixing. Preferably additional mixing is provided, e.g. by using a stirrer or using a pump-around circuit or applying a combination of both.

The reaction mixture obtained in the first reaction zone is then guided to the second reaction zone, in which second reaction zone the temperature is equal to or—preferred—higher than the temperature in the first reaction zone, but not more than 20° C. higher (preferably not more than 10° C., even more preferably not more than 5° C. higher). A temperature in the second of the n reaction zones which is at least 2° C. higher than the temperature in the first reaction zone is particularly preferred. In other words, the temperature rise from the first to the second of the n reaction zones is preferably of from 2° C. to 20° C., more preferably of from 2° C. to 10° C., and particularly preferably of from 2° C. to 5° C.

The second portion of aqueous formaldehyde is added to this second of the n reaction zones. As a result of the inventive concept of adding a second portion of formaldehyde to the second reactor, exothermal processes take place therein, so that adjusting the temperature in the second reaction zone requires cooling. This is preferably achieved by evaporative cooling just as in the first reaction zone (see above). More particularly, water is evaporated from the reaction mixture, condensed and—at least partially—fed back to the reaction zone at a pressure lower than ambient pressure. The temperature can thus easily be adjusted by choice of an appropriate pressure. The second reaction zone is operated without or with additional mixing. Preferably additional mixing is provided, e.g. by using a stirrer or using a pump-around circuit or applying a combination of both.

In order to allow for a sufficient reaction progress before addition of the second portion of formaldehyde, it is preferred that said addition should take place 10 minutes to 60 minutes, preferably 15 minutes to 45 minutes, after the initial contacting of aniline hydrochloride with the first portion of aqueous formaldehyde in step (1b) or the initial contacting of the aminal with hydrochloric acid in step (1d), whichever is applicable. In the preferred continuous operation mode, this corresponds to an average residence time of the stream of the reacting mixture from (i) the initial contacting of aniline hydrochloride with the first portion of aqueous formaldehyde in step (1b) or the initial contacting of the aminal with hydrochloric acid in step (1d) to (ii) the initial addition of the second portion of formaldehyde of from 10 minutes to 60 minutes, preferably of from 15 minutes to 45 minutes.

The reaction mixture from the second reaction zone is guided to the third reaction zone and so forth. According to the invention, the temperature consecutively increases from the third to the $n^{th}$ of the reaction zones, the temperature in the third of the n reaction zones being from 15° C. to 50° C. higher than in the second of then reaction zones. The temperature rise is accomplished by heating, for example by using reactors equipped with a heating jacket.

There are at least 4 reaction zones and up to 25. Preferably, n equals 15 (corresponding to a cascade of 4 to 15 reaction zones), more preferably 12 (corresponding to a cascade of 4 to 12 reaction zones), more preferably 10 (corresponding to a cascade of 4 to 10 reaction zones), and most preferably 8 (corresponding to a cascade of 4 to 8 reaction zones). Preferably, the temperature in the $n^{th}$ of the n reaction zones is from 120° C. to 200° C.

As regards the apparatuses used for step (2), any of the reactors known in the art for the rearrangement step in MDA production can be used, for example reactors without mixing, stirred reactors, reactors with pump-around circuit, segmented or unsegmented tubular reactors. The reactor can be equipped with installations such as for example baffles of sieve trays. Then reaction zones can simply be the inner volume of n reactors (arranged in series and in particular connected to each other via pipes, flanges, valves or the like) that is available for chemical reactions in the liquid phase, i.e. the n reaction zones are located in n reactors in this embodiment. Alternatively, it is also possible that the n reactions zones are located in less than n reactors, at least one of the less than n reactors comprising at least two reaction zones which are sequentially run through by the first reaction product and which reaction zones can be controlled independently (as regards the temperature). The transition from one reaction zone to the next in one and the same reactor can, in the simplest case, just be characterized by an increase in temperature. It is, however, also possible that the point of transition is characterized by physical means such as internals, flanges or valves that are positioned between two reaction zone.

Step (3) of the invention can be conducted as known in principle from the prior art. The second reaction product comprising the di- and polyamines of the diphenylmethane series is neutralized by adding a suitable base. Suitable bases are, for example, the hydroxides of the alkali metal and alkaline earth metal elements, preferably of the alkali metal elements, such as sodium hydroxide or potassium hydroxide, preferably sodium hydroxide. The base is in particular used as aqueous solution. Optionally, extra water and/or aniline is added in this step. The neutralization is typically effected at temperatures of, for example, 90.0° C. to 120.0° C. without addition of further substances. It can alternatively be effected at a different temperature level in order, for example, to accelerate the degradation of troublesome by-products. The base used for neutralization is preferably used in amounts of greater than 100%, more preferably 105% to 120%, of the amount stoichiometrically required for the neutralization of the acidic catalyst used (see EP 1 652 835 A1).

The neutralized reaction mixture comprising the di- and polyamines of the diphenylmethane series is separated into an organic phase comprising di- and polyamines of the diphenylmethane series and an aqueous phase. This can be assisted by the addition of aniline and/or water. If the phase separation is assisted by addition of aniline and/or water, they are preferably added already with vigorous mixing in the neutralization. The mixing can be effected here in mixing zones with static mixers, in stirred tanks or stirred tank cascades, or else in a combination of mixing zones and stirred tanks.

The organic phase obtained in the phase separation is preferably washed in a washing unit with washing liquid (preferably water), followed by separating the mixture obtained in in a separation unit into an organic phase comprising di- and polyamines of the diphenylmethane series and an aqueous phase. The organic phase is preferably distilled to obtain the di- and polyamines of the diphenylmethane series as a sump product, with removal of a distillate stream comprising water and aniline. The distillation is preferably carried out in at least two steps, e.g. in case of a two-step distillation set-up removing part of the aniline and water a flash distillation, a distillation column or any other suitable distillation device and removing the remainder of aniline and water in a second distillation step e.g. using a distillation column or any other suitable distillation device.

The sump stream comprising the di- and polyamines of the diphenylmethane series is suitable for phosgenation to MDI of high quality.

The invention will be illustrated in detail below with the aid of examples.

EXAMPLES

Analytical Methods Employed:
The composition of the MDA was determined using reversed phase HPLC.
In case of the MDI samples:
viscosity was determined at 25° C. either using a falling ball viscosimeter or a rotational viscosimeter;
the color was determined by measuring the absorbance (at 430 nm and 520 nm, respectively) of a 2% solution of MDI in pure MCB using a UV/VIS photometer;
the NCO-content was determined by reacting MDI with an excess of dibutylamine and back-titration with standardized HCl solution.

Example 1: Continuous Process without Formaldehyde Split (Comparative)

In a continuous reaction process, 18.0 t/h of feed aniline (containing 90.0% by mass of aniline) and 8.0 t/h of 32% aqueous formaldehyde solution (corresponding to a molar ratio of aniline:formaldehyde of 2.0:1 were mixed and converted to the aminal at a temperature of 80° C. and a pressure of 1.40 bar (absolute) in a stirred reaction tank R0. The reaction tank R0 was provided with a cooler having a cooling circuit pump. The reaction mixture leaving the reaction tank R0 was guided into a phase separation apparatus (aminal separator). This corresponds to step (1c) with the exception that, in contrast to the inventive process, the entire amount of formaldehyde to be used was added to the reactor R0.

After the phase separation to remove the aqueous phase, the organic phase was admixed in a mixing nozzle with 30% aqueous hydrochloric acid (protonation level 9.2%, i.e. 0.092 mole of HCl was added per mole of amino groups—step (1d)) and run into the first rearrangement reactor R1. The first rearrangement reactor R1 (called "vacuum tank") was operated at 48.0° C., which was ensured by means of evaporative cooling in a reflux condenser at a pressure of 104 mbar (absolute). The reflux condenser was charged with 0.50 t/h of fresh aniline (resulting in an overall molar ratio of aniline:formaldehyde of 2.1:1).

The reaction to MDA of the thus obtained first reaction product was conducted to completion in a reactor cascade composed of seven further rearrangement reactors R2 to R8 (i.e. in a total of eight rearrangement reactors R1 to R8) at 53° C. to 153° C. (i.e. 53° C. in reactor R2/90° C. in reactor R3/109° C. in reactor R4/119° C. in reactor R5/135° C. in reactor R6/147° C. in reactor R7/153° C. in reactor R8). This corresponds to step (2) with the exception that, in contrast to the inventive process, no second portion of formaldehyde was added to the second rearrangement reactor R2.

On completion of reaction, the reaction mixture obtained (=second reaction product) was admixed with 32% sodium hydroxide solution in a molar ratio of 1.10:1 sodium hydroxide to HCl and reacted in a stirred neutralization vessel. The temperature in the neutralization vessel was 115.0° C. and the absolute pressure was 1.40 bar. The neutralized reaction mixture was then separated in a neutralization separator into an aqueous lower phase, which was guided to a wastewater collection vessel, and into an organic upper phase.

The organic upper phase was guided to a washing section and washed with condensate in a stirred washing vessel. After the washing water was separated from the biphasic mixture obtained in the washing vessel in a washing water separator, the crude MDA thus obtained was freed of water and aniline by distillation, and the final MDA was obtained as bottom product (step (3)).

The results of the comparative example 1 including the results of the corresponding test phosgenation according to the general procedure provided below are summarized in Table 1.

When the MDA from comparative example 1 was transformed to MDI in a continuous phosgenation process, a product was obtained as sump product of a distillation step in which monomeric MDI was partly separated off, which product showed the following analytical properties:

viscosity @ 25° C.: 642 mPa·s;
NCO: 30.7 weight-%;
Total chlorine content: 1453 ppm.

Example 2: Continuous Process with Formaldehyde Split to the Second Reactor R1 (Comparative)

In a continuous reaction process, 22.4 t/h of feed aniline (containing 96% by mass of aniline) and 9.7 t/h of 32% aqueous formaldehyde solution (corresponding to a molar ratio of aniline:formaldehyde of 2.23:1 were mixed and converted to the aminal at a temperature of 90° C. and a pressure of 1.05 bar (absolute) in an adiabatically operated stirred reaction tank R0. The reaction mixture leaving the reaction tank R0 was guided into a phase separation apparatus (aminal separator). This corresponds to step (1c).

After the phase separation to remove the aqueous phase, the organic phase was admixed in a mixing nozzle with 0.5 t/h of 32% aqueous formaldehyde solution and fed to the first rearrangement reactor R1. A separate nozzle fed 2.5 t/h of 31.5% aqueous hydrochloric acid (protonation level 9%, i.e. 0.09 mole of HCl was added per mole of amino groups—step (1d)) into the first rearrangement reactor R1 (called "vacuum tank") which was operated at 52° C., ensured by means of evaporative cooling in a reflux condenser at a pressure of 130 mbar (absolute). The reflux condenser was charged with 0.80 t/h of fresh aniline (resulting in an overall molar ratio of aniline:formaldehyde of 2.2:1).

The reaction to MDA of the thus obtained first reaction product was conducted to completion in a reactor cascade composed of four further rearrangement reactors R2 to R5 (i.e. in a total of five rearrangement reactors R1 to R5) at 91° C. to 152° C. (i.e. 91° C. in reactor R2/134° C. in reactor R3/147° C. in reactor R4/152° C. in reactor R5). This corresponds to step (2) with the exception that, in contrast to the inventive process, the second portion of formaldehyde was added to the first rearrangement reactor R1 instead of the second reactor R2.

On completion of reaction, the reaction mixture obtained (=second reaction product) was admixed with 50% sodium hydroxide solution in a molar ratio of 1.10:1 sodium hydroxide to HCl and reacted in a stirred neutralization vessel. The temperature in the neutralization vessel was 106° C. and the absolute pressure was 1.05 bar. The neutralized reaction mixture was then separated in a neutralization separator into an aqueous lower phase, which was guided to a wastewater collection vessel, and into an organic upper phase.

The organic upper phase was guided to a washing section and washed with condensate in a stirred washing vessel. After the washing water was separated from the biphasic mixture obtained in the washing vessel in a washing water separator, the crude MDA thus obtained was freed of water and aniline by distillation, and the final MDA was obtained as bottom product (step (3)).

The results of the comparative example 2 including the results of the corresponding test phosgenation according to the general procedure provided below are summarized in Table 1.

Example 3: Continuous Process with Formaldehyde Split to the Second Reactor R2 (According to the Invention)

In a continuous reaction process, 18.0 t/h of feed aniline (containing 90.0% by mass of aniline) and 5.6 t/h of 32% aqueous formaldehyde solution (corresponding to a molar ratio of aniline:formaldehyde of 2.9:1 were mixed and converted to the aminal at a temperature of 80° C. and a pressure of 1.40 bar (absolute) in a stirred reaction tank R0 (step (1c)). The reaction tank R1 was provided with a cooler having a cooling circuit pump. The reaction mixture leaving the reaction tank R0 was guided into a phase separation apparatus (aminal separator).

After the phase separation to remove the aqueous phase, the organic phase was admixed in a mixing nozzle with 30% aqueous hydrochloric acid (protonation level 9.2%, i.e. 0.092 mole of HCl was added per mole of amino groups—step (1d)) and run into the first rearrangement reactor R1. The first rearrangement reactor R1 (called "vacuum tank") was operated at 48.0° C., which was ensured by means of evaporative cooling in a reflux condenser at a pressure of 104 mbar (absolute). The reflux condenser was charged with 0.50 t/h of fresh aniline (resulting in an overall molar ratio of aniline:formaldehyde of 3.0:1 in R1).

In the second rearrangement reactor R2, 2.4 t/h of 32% aqueous formaldehyde solution was added to the reaction mixture coming from R1 (resulting in an overall molar ratio of aniline:formaldehyde of 2.1:1 in R2). The average residence time of the reaction mixture from the initial contacting of aminal and hydrochloric acid in step (1d) to the initial addition of the second portion of formaldehyde was approximately 30 minutes. At this point the formaldehyde split was 30%. R2 was operated at 53° C. The temperature was maintained by evaporative cooling.

The reaction to MDA was conducted to completion in a reactor cascade composed of a total of six additional reactors R3 to R8 (i.e. in a total of eight rearrangement reactors R1 to R8) at 90° C. to 153° C. (90° C. in reactor R3/109° C. in reactor R4/119° C. in reactor R5/135° C. in reactor R6/147° C. in reactor R7/153° C. in reactor R8)—step (2).

On completion of reaction, the reaction mixture obtained was admixed with 32% sodium hydroxide solution in a molar ratio of 1.10:1 sodium hydroxide to HCl and reacted in a stirred neutralization vessel. The temperature in the neutralization vessel was 115.0° C. and the absolute pressure was 1.40 bar. The neutralized reaction mixture was then separated in a neutralization separator into an aqueous lower phase, which was guided to a wastewater collection vessel, and into an organic upper phase.

The organic upper phase was guided to the washing section and washed with condensate in a stirred washing vessel. After the washing water was separated from the biphasic mixture obtained in the washing vessel in a washing water separator, the crude MDA thus obtained was freed of water and aniline by distillation, and the final MDA was obtained as bottom product (step (3)).

The results of the example 3 including the results of the corresponding test phosgenations according to the general procedure provided below are summarized in Table 1.

When the MDA from example 3 (according to the invention) was transformed to MDI in a continuous phosgenation process, a product was obtained as sump product of a distillation step in which monomeric MDI was partly separated off, which product showed the following analytical properties:

viscosity @ 25° C.: 682 mPa·s;
NCO: 30.9 weight-%;
Total chlorine content: 1138 ppm.

Compared to example 1 (comparative), at comparable viscosities and NCO values, the total chlorine content was significantly reduced.

General Procedure for Test-Phosgenation (Lab-Scale, Batch):

Starting Materials:
MDA obtained by acid-catalyzed condensation of aniline with formaldehyde
Anhydrous chlorobenzene
Phosgene 15 g of the MDA prepared according to the above examples was dissolved in 70 ml of chlorobenzene, heated to 55° C. and poured into a solution of 32 g of phosgene in 80 ml of chlorobenzene at a temperature of 0° C. within 10 s with intensive stirring. The suspension was heated to 100° C. within 45 minutes by passing through phosgene and then heated to reflux temperature for 10 minutes. After a further 10 minutes at this temperature, the solvent was distilled off under reduced pressure down to a bottom temperature of 100° C. The crude isocyanate was then heated in a distillation apparatus at a pressure of 4 to 6 mbar by means of a hot air blower until the first product started distilling and then cooled to room temperature within 5 to 10 minutes. Of the isocyanate obtained in this way, 1.0 g was dissolved in chlorobenzene and diluted with chlorobenzene to 50 ml. The absorption of the solution obtained in this way was determined at the two wavelengths of 430 nm and 520 nm. A Dr. Lange LICO 300 photometer was used as the measuring instrument.

(1c) mixing aniline with a first portion of aqueous formaldehyde to form an aminal, and
(1d) mixing the aminal with hydrochloric acid;
to obtain a first reaction product;
(2) converting the first reaction product to a second reaction product comprising di- and polyamines of the diphenyl methane series in a cascade of 4 to n reaction zones arranged in series, n being a natural number of from 4 to 25, wherein a second portion of aqueous formaldehyde is added to the second of the n reaction zones, which second reaction zone is at a temperature that is equal to or up to 20° C. higher than the temperature in the first reaction zone, and wherein the temperature consecutively increases from the third to the $n^{th}$ of the reaction zones, the temperature in the third of then reaction zones being from 15° C. to 50° C. higher than in the second of the n reaction zones, and
(3) working-up the second reaction product to obtain the di- and polyamines of the diphenyl methane series.

2. The process of claim 1, wherein the first portion of aqueous formaldehyde comprises 50% to 90% of all formaldehyde ($CH_2O$) used in the process, wherein the percentages refer to moles of formaldehyde ($CH_2O$).

3. The process of claim 2, wherein the second portion of aqueous formaldehyde comprises 10% to 50% of all formaldehyde ($CH_2O$) used in the process, wherein the percentages refer to moles of formaldehyde ($CH_2O$).

4. The process of claim 1, wherein the molar ratio of aniline to the total amount of formaldehyde used in the process is from 1.5:1 to 10:1.

5. The process of claim 1, to wherein the aqueous formaldehyde comprises, in relation to its total mass, a proportion by mass of formaldehyde of from 30% to 60%.

6. The process of claim 1, wherein the temperature in the first of then reaction zones is from 30° C. to 70° C.

7. The process of claim 6, wherein the temperature in the first of then reaction zones is adjusted by evaporating, condensing and feeding-back of water at a pressure lower than ambient pressure.

8. The process of claim 1, wherein the temperature in the $n^{th}$ of the n reaction zones is from 120° C. to 200° C.

9. The process of claim 1, wherein n equals 15.

TABLE 1

Experimental results (continuous MDA process and batch test phosgenations)

| | MDA | | | MDI | | | |
|---|---|---|---|---|---|---|---|
| Example | Sum 2-ring MDA [weight-%] | N-methyl-4,4'-MDA [weight-%] | N-formyl-4,4'-MDA [weight-%] | E 430 | E520 | Viscosity @ 25° C.[a] [mPas] | NCO [weight-%] |
| 1 (comp.) | 54.5 | 0.28 | 0.28 | 0.104 | 0.023 | 94 | 32.4 |
| 2 (comp.) | 53.7 | 0.29 | 0.31 | 0.131 | 0.030 | 123 | 32.4 |
| 3 (inventive) | 54.5 | 0.17 | 0.14 | 0.075 | 0.012 | 94 | 32.4 |

[a]In contrast to the continuous phosgenations described above, no monomeric MDI was distilled off after phosgenation, resulting in lower viscosities of the MDI produced.

The invention claimed is:

1. A process for preparing di- and polyamines of the diphenyl methane series, comprising:
(1) reacting aniline and formaldehyde by
(1a) mixing aniline with hydrochloric acid to form aniline hydrochloride, and
(1b) mixing the aniline hydrochloride with a first portion of aqueous formaldehyde;
or 10. The process of claim 1, wherein n equals 12.

11. The process of claim 1, wherein n equals 10.

12. The process of claim 1, wherein n equals 8.

13. The process of claim 1, wherein the n reaction zones are located in n reactors.

14. The process of claim 1, wherein the n reaction zones are located in less than n reactors, at least one of the less than n reactors comprising at least two reaction zones which are sequentially run through by the first reaction product.

15. The process of claim 1, wherein, after mixing aniline with the first portion of aqueous formaldehyde in (1c), a two-phase mixture is formed which is separated into an aqueous phase and an organic phase comprising the aminal, which organic phase is mixed with hydrochloric acid in (1d).

16. The process of claim 1, wherein (1b) or (1d) are carried out in the first reaction zone.

17. The process of claim 1, wherein (1b) or (1d) are carried out in an apparatus upstream of the first reaction zone.

18. The process of claim 1, wherein the addition of the second portion of formaldehyde is carried out 10 minutes to 60 minutes after the initial contacting of aniline hydrochloride with the first portion of aqueous formaldehyde in step (1b) or the initial contacting of the aminal with hydrochloric acid in step (1d).

19. The process of claim 1, wherein the temperature of the second of the n reaction zones is higher than the temperature in the first reaction zone.

20. The process of claim 19, wherein the temperature of the second of then reaction zones is at least 2° C. higher than the temperature in the first reaction zone.

21. The process of claim 1, wherein at least step (2) is carried out continuously.

\* \* \* \* \*